United States Patent
Sherman

[11] Patent Number: 6,156,279
[45] Date of Patent: *Dec. 5, 2000

[54] METHOD OF AND APPARATUS FOR MANUFACTURING METHANOL

[75] Inventor: Jeffrey H. Sherman, Dallas, Tex.

[73] Assignee: GRT, Inc., Dallas, Tex.

[ * ] Notice: This patent is subject to a terminal disclaimer.

[21] Appl. No.: 09/370,945

[22] Filed: Aug. 9, 1999

Related U.S. Application Data

[60] Division of application No. 09/224,394, Dec. 31, 1998, and a continuation-in-part of application No. 09/058,494, Apr. 10, 1998, Pat. No. 5,954,925.

[51] Int. Cl.[7] .................................................. B01J 19/08

[52] U.S. Cl. ........................................ 422/186; 422/186.3

[58] Field of Search ................................. 422/186.3, 186

[56] References Cited

U.S. PATENT DOCUMENTS

| | | | |
|---|---|---|---|
| 3,773,659 | 11/1973 | Carlson et al. | 210/7 |
| 3,845,317 | 10/1974 | Lindwall et al. | 422/186.3 |
| 4,069,147 | 1/1978 | Abrams et al. | 210/6 |
| 4,132,637 | 1/1979 | Key et al. | 210/7 |
| 4,287,070 | 9/1981 | Pollock | 210/626 |
| 4,311,570 | 1/1982 | Cowen et al. | 422/186 |
| 4,624,791 | 11/1986 | Ferriss | 210/704 |
| 4,861,471 | 8/1989 | Nakao et al. | 210/182 |
| 4,888,101 | 12/1989 | Cooper | 204/157.15 |
| 4,966,759 | 10/1990 | Robertson et al. | 422/186 |
| 4,968,429 | 11/1990 | Yen | 210/637 |
| 5,156,173 | 10/1992 | Keyser et al. | 134/61 |
| 5,254,253 | 10/1993 | Behmann | 210/607 |
| 5,271,810 | 12/1993 | Keyser et al. | 202/185 |
| 5,316,682 | 5/1994 | Keyser et al. | 210/649 |
| 5,510,544 | 4/1996 | Keyser | 570/125 |
| 5,529,701 | 6/1996 | Grisham et al. | 210/787 |
| 5,531,904 | 7/1996 | Grisham et al. | 210/703 |
| 5,658,458 | 8/1997 | Keyser et al. | 210/195 |
| 5,662,811 | 9/1997 | Grisham et al. | 210/788 |
| 5,720,858 | 2/1998 | Noceti et al. | 204/157.6 |

OTHER PUBLICATIONS

Article titled "Semiconductor Photocatalysis" by Claire Jones found on the internet at www.warwick.ac.uk/~msrjn/fsemic.html.

Article titled "Factors Affecting Photocatalysis on Mesoporous Titanium Dioxide" by Victor Frank Stone, Jr. dated 1997 found on the internet at wwwl.che.ufl.edu/meeting/1997/annual/session/275/y/index.html.

Article titled "Solar Chemical Process Engineering" found on the internet at http://chemengineer.tqn.com/library/weekly/aa06397.htm.

Article titled "Titanium Dioxide Photocatalysis: Developing Remediation Technology for Multiple Wastes" By Tricia Drol found on the internet at http://geology.wright.edu/geology/cgwm/iris/Waterline/page9.html.

Article titled "Photochemical Treatment of Pollutants" found on the internet at http://www.nrel.gov/research/industrialtech/pollution.html.

Article titled "Through a glass, not so darkly" found on the internet at http://ci.mond.org/9518/951811.html.

Article titled "Green Technology for the 21st Century Photocatalysts" found on the internet at http://www.engr.wisc.edu/interd/wcp/Photocatalysts.html.

(List continued on next page.)

*Primary Examiner*—Kathryn Gorgos
*Assistant Examiner*—Thao Tran
*Attorney, Agent, or Firm*—Michael A. O'Neil

[57] ABSTRACT

In a method of and apparatus for manufacturing methanol from methane, a catalytic area is formed on the exterior of a hollow sintered stainless steel tube. Methane is maintained within the sintered stainless steel tube at predetermined pressure, and water continuously flowing across the exterior surface thereof strips the methane forming sub-micron sized methane bubbles. Light energy is directed onto the catalytic surface to form hydroxyl radicals from the flowing water. The hydroxyl radicals cleave the carbon-hydrogen bonds of the methane to form methyl ions which combine with the hydroxyl ions to form methanol.

6 Claims, 3 Drawing Sheets

OTHER PUBLICATIONS

Article entitled "Photochemical Conversion of Methane" from the Journal of Molecular Catalysis, pp. 371–379 by Kotaro Ogura and Makoto Kataoka, No Date Available.

Article entitled "Conversion of Methane to Oxygen–Containing Compounds by the Photochemical Reaction" from Ind. Eng. Chem. Reg., pages 1387–1390 by Kotaro Ogura, Catharina T. Migita and Minoru Fujita, No Date Available.

Article entitled "Hydrogen Generation Using Cu(II)/WO3 and Oxalic Acid by Visible Light" from Hydrogen Energy, pages 677–680 by P. Maruthamuthu and M. Ashokkumar, No Date Available.

Article entitled "Hydrogen Production with Visible Light Using Metal Loaded–WO3 and MV2+ in Aqueous Medium" from Hydrogen Energy, pp. 275–277 by P. Maruthamuthu and M. Ashokkumar, No Date Available.

Article entitled "Photocatalytic Hydrogen Production with Semiconductor Particulate Systems: An Effort to Enhance the Effeciency" from Int. J. Hydrogen Energy, pp. 591–595 by P. Maruthamuthu and M. Ashokkumar, No Date Available.

Article entitled "Doping Effects of Transition Metal Ions on the Photosensitization of WO3 Particles" from Solar Energy Materials, pp. 433–438 by Pichai Maruthamuthu and Muthupandian Ashokkumar, No Date Available.

Articled entitled "Factors Influencing the Photocatalytic Efficiency of WO3 Particles" from Journal of Photochemistry and Photobiology, A: Chemistry, pp. 249–258 by M. Ashokkumar and P. Maruthamuthu, No Date Available.

Article entitled "Visible Light Induced Water Cleavage in Colloidal Solutions of Chromium–Doped Titanium Dioxide Particles" from J. Am. Chem. Soc., pp. 2996–3002 by Enrico Borgarello, John Kiwi, Michael Gratzel, Ezio Pelizzetti and Mario Visca, No Date Available.

Article entitled "Electron Transfer Reactions and Flat–Band Potentials of WO3 Colloids" from J. Phys. Chem., pp. 5827–5830 by M.T. Nenadovic, T. Rajh, O.I., Mieie, and A.J. Nozik, No Date Available.

Article titled "Pplatinum Catalysts– for the High–Yield Oxidation od Methane to a Methanol Derivative" by Roy A. Periana dated May 24, 1998 published in Science vol. 280, No Date Available.

Article titled Progess Report: Investigation of the Partial Oxidation of Methane to Methanol in a Simulated Countercurrent Moving Bed Reactor bythe National Center For Environmental Research And Quality Assurance, No Date Available.

Article titled "Photocatalytic Degradation of 2–Chlorophenol in TiO2 Aqueous Suspension: Modeling of Reaction Rate" by L Rideh publsihed 1997 in American Chemical Society, No Month Available.

Article titled "Photocatalytic Degradation of Water Organic pollutants. Kinetic modeling and Energy Efficiency" by B. Serrano published 1997 in American Chemical Society, No Date Available.

Article titled "Simplified Modeling of Radiant Fields in Heterogeneous Photoreactors.1.Case of Zero Reflectance" by Alberto Bucato published 1997 Amercian Chemical Society, No Month Available.

Article titled "Cylindrical Photocatalytic Reactors. Radiation Absorption and Scattering Effects Produced by Suspended Fine Particle in an Annular Space" by Roberto L. Romero published 1997 American Chemical Society, No Month Available.

Article titled "Efficient photo–assisted Fenton catalysis mediated by Fe ions on Nafion membranes active in the abatement of non–biodegradable azo–dye" by Javier Fernandez published 1998 in Chemical Commun, No Month Available.

Article titled "Kinetic Analysis of the Photocatalytic Degradation of Gas–Phase 2–propanol under Mass Transport–Limited Conditions with a TiO2 Film Photocatalyst" by Yoshihisa Ohko published 1998 in the J. Physi. Chem, No Month Available.

Article titled "Time–Dependent Behavior of Active Oxygen Species Formed on Photoirradiated TiO2 Films in Air" by Ken–ichi–Ishibashi published March 19, 1998 in vol. 102, No. 12 of the Journal of Physical Chemistry B, No Month Available.

Article titled "Kinetics of Photocatalytic Reactions under extremely Low Intensity UV Illumination of Titanium Dioxide Thin Films" by Yoshihisa Ohko published 1997 J. Phys.Chem A, No Month Available.

Article titled "Preparation of a New Nanostructured TiO2 Surface Using a Two–Dimensional Array–Based Template" by Sachiko Matsushita published 1997 in The Chemical Society of Japan, No Month Available.

Article titled "Electronic Structure of Discrete Pseudotetrahedral Oxovanadium Centers Dispersed ina Silica Xerogel Matrix: Implications for Catalysis and Photocatalysis" by Kim Tran published 1995 in American Chemical Journal, No Month Available.

Article titled "Water Purification by Simiconductor Photocatalysis" by Andrew Mills publsihed 1993 in Chemcial Society Reviews, No Month Available.

Article titled "Low–Temperature Nonoxidative Activation of Methane over H–Galloaluminsilicate (MFI) Zeolite" by Vasant R. Choudhary published Feb. 1997 by the American Assocation for the Advancement of Science, No Month Available.

METHOD OF AND APPARATUS FOR MANUFACTURING METHANOL

CROSS REFERENCE TO RELATED APPLICATION

This is a division of U.S. application Ser. No. 09/224,394, filed Dec. 31, 1995, still pending.

This application is a continuation-in-part of prior application Ser. No. 09/058,494, filed Apr. 10, 1998, now U.S. Pat. No. 5,954,925.

TECHNICAL FIELD

This invention relates generally to the manufacture of methanol, and more particularly to a method of and apparatus for manufacturing methanol from methane.

BACKGROUND

Methanol, the simplest of the alcohols, is a highly desirable substance which is useful as a fuel, as a solvent, and as a feedstock in the manufacture of more complex hydrocarbons. In accordance with the method of methanol manufacture that is currently practiced in the petroleum industry, methane is first converted to synthesis gas, a mixture of carbon monoxide and hydrogen. The synthesis gas is then converted over an alumina-based catalyst to methanol. The formation of synthesis gas from methane is an expensive process.

As will be apparent, methane and methanol are closely related chemically. Methane comprises a major component of natural gas and is therefore readily available. Despite the advantages inherent in producing methanol directly from methane, no commercially viable system for doing so has heretofore been developed.

SUMMARY OF THE INVENTION

The present invention comprises a method of and apparatus for manufacturing methanol from methane which overcomes the foregoing and other deficiencies which have long since characterized the prior art. The method involves a semipermeable partition upon which a light-activated catalyst capable of producing hydroxyl radicals from water is deposited. Water is passed over the catalyst side of the porous surface and methane at a positive pressure is present on the opposite side of the surface. The catalyst is exposed to light while water is passed over the catalyst. The light-exposed catalyst reacts with the water molecules to form hydroxyl radicals. The methane gas is forced through the semipermeable partition forming small bubbles in the flowing water. The hydroxyl radicals in the water can then undergo a free-radical reaction with the methane gas in the water to form methanol.

In accordance with the broader aspects of the invention there is generated a stream of sub-micron sized methane bubbles. Due to their extremely small size, the methane bubbles have an extremely large surface area which increases reaction efficiency. Smaller pores in the semipermeable partition facilitate the formation of smaller bubbles. Additionally, higher water velocity across the catalytic surface aids in shearing the bubbles off the surface while they are still small.

In accordance with more specific aspects of the invention, a porous sintered stainless steel tube has an exterior coating comprising a titanium-based catalyst. The sintered stainless steel tube is positioned within a glass tube and water is caused to continuously flow through the annular space between the two tubes. Methane is directed into the interior of the sintered stainless steel tube and is maintained at a pressure high enough to cause methane to pass into the water and prevent the flow of water into the interior of the stainless steel tube. As the water passes over the stainless steel tube, methane bubbles are continually sheared off of the sintered surface. The methane bubbles thus generated are sub-micron in size and therefore present an extremely large surface area.

Ultraviolet light energy generated from ultraviolet lamps is directed through the glass tube and engages the titanium-based catalyst to generate hydroxyl radicals in the flowing water. The hydroxyl radicals undergo a free-radical reaction with the methane forming methanol, among other free-radical reaction products. Subsequently, the methanol is separated from the reaction mixture by distillation.

BRIEF DESCRIPTION OF THE DRAWINGS

A more complete understanding of the invention may be had by reference to the following Detailed Description when taken in conjunction with the accompanying Drawings wherein.

DETAILED DESCRIPTION

Figure 1:
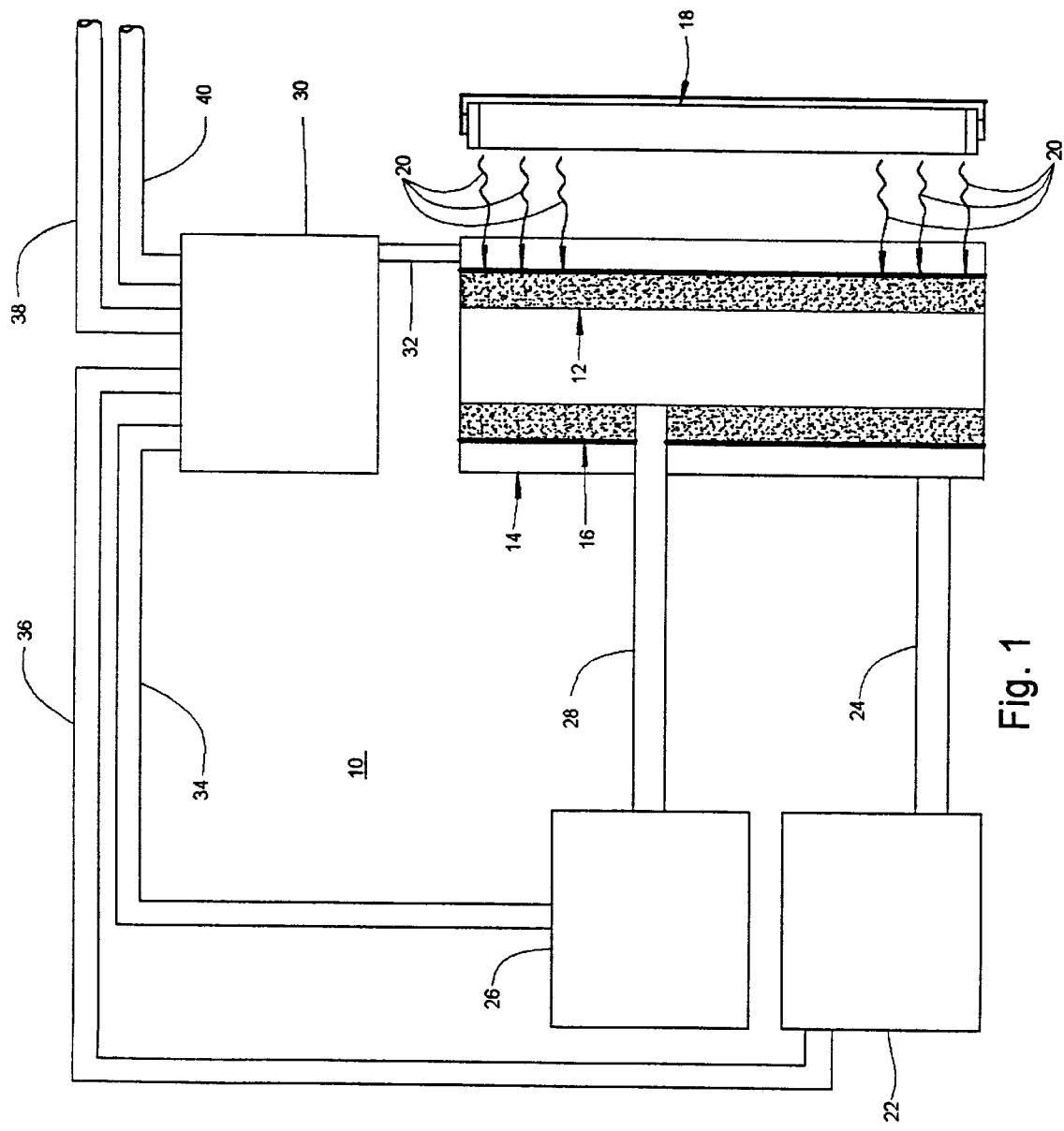
FIG. 1 is a diagrammatic illustration of a method and apparatus for manufacturing methane comprising a first embodiment of the present invention.

Referring now to the Drawings, and particularly to FIG. 1 thereof, there is shown an apparatus for manufacturing methanol 10 comprising a first embodiment of the invention. The apparatus 10 includes a sintered stainless steel tube 12 positioned within a glass tube 14. As illustrated in FIG. 1, both the sintered stainless steel tube 12 and the glass tube 14 comprise right circular cylinders with the tube 12 extending concentrically relative to the tube 14. Other geometrical configurations of and positional relationships between the sintered stainless steel tube 12 and the glass tube 14 may be utilized in accordance with the requirements of particular applications of the invention.

The sintered stainless steel tube 12 has a catalyst layer 16 formed on the exterior surface thereof. The catalyst layer 16 is preferably a titanium-based catalyst; however, it will be understood that any light-activated catalyst which forms hydroxyl radicals from water may be utilized in the practice of the invention, if desired. A plurality of ultraviolet lamps 18 are positioned around the exterior of the glass tube 14, it being understood that while only one lamp 18 is illustrated in FIG. 1, in actual practice a plurality of lamps 18 are employed and are disposed around the entire periphery of the tube 14. As illustrated by the waves 20 in FIG. 1, the ultraviolet lamps 18 generate energy in the form of ultraviolet light which is directed through the glass tube 14 and onto the catalyst layer 16 formed on the exterior surface of the sintered stainless steel tube 12.

In the operation of the apparatus for manufacturing methanol 10, a quantity of water is received in a reservoir 22. Water from the reservoir 22 is directed into the annular space between the sintered stainless steel tube 12 and the glass tube 14 through piping 24. During the operation of the apparatus 10 water flows through the annulus between the sintered stainless steel tube 12 and the glass tube 14 on a continuous basis.

A quantity of methane is stored in a reservoir 26. In the operation of the apparatus 10, methane is directed from the reservoir 26 into the interior of the sintered stainless steel tube 12 through piping 28. The methane within the sintered stainless steel tube 12 is maintained at a pressure high enough to cause methane to pass through the walls of the sintered stainless steel tube 12 into the water and prevent the flow of water into the interior of the tube 12.

In the operation of the apparatus for manufacturing methanol 10, the water flowing through the annular space between the sintered stainless steel tube 12 and the glass tube 14 causes methane bubbles to be continuously stripped off the sintered stainless steel surface of the tube 12. In this manner the size of the methane bubbles is maintained in the sub-micron range. The sub-micron size of the methane bubbles provides an enormous methane surface area which in turn results in unprecedented reaction efficiency.

As the sub-micron size methane bubbles are produced by the flow of water over the exterior surface of the sintered stainless steel tube 12, ultraviolet light energy from the lamps 18 continuously engages the catalyst layer 16 formed on the exterior of the tube 12. This generates hydroxyl radicals in the flowing water. The hydroxyl radicals homolytically cleave one or more of the carbon-hydrogen bonds in the methane thereby forming either molecules of hydrogen or molecules of water, depending upon the initiating radical, and methyl radicals. The methyl radicals combine either with the hydroxyl radicals to form methanol or with the hydrogen radicals to form methane.

Those skilled in the art will appreciate the fact that other chemical reactions are possible in the operation of the apparatus for manufacturing methanol 10. For example, there exists the possibility of a methyl-methyl radical reaction, and also the possibility of a hydrogen-hydrogen radical reaction. Both of these possibilities are extremely remote due to the relatively low concentrations of methyl radicals and hydrogen radicals at any given time.

The water flowing from the annulus between the sintered stainless steel tube 12 and the glass tube 14 having the reaction products contained therein is directed to a distillation apparatus 30 through piping 32. The distillation apparatus 30 separates the outflow from the space between the tube 12 and the tube 14 into at least four streams, including a stream of unreacted methane 34 which is returned to the reservoir 26, a stream of water 36 which is returned to the reservoir 22, a stream of other reaction products 38 which are recovered, and a stream of methanol 40. The stream of other reaction products 38 may be further separated into its component parts, if desired.

The present invention further comprises a method of making methanol. In accordance with the method there is provided a continuously flowing stream of water. Sub-micron size bubbles of methane are continuously injected into the flowing water. Hydroxyl radicals are continuously generated from the water. The hydroxyl radicals cleave the hydrogen-carbon bonds of the methane to form methyl radicals. The methyl radicals combine with the hydroxyl radicals to form methanol.

In accordance with more specific aspects of the method, a sintered stainless steel tube having a titanium-based catalytic layer on the exterior surface thereof is positioned within a glass tube. Water is directed through the annulus between the sintered stainless steel tube and the glass tube, and methane is directed into the interior of the sintered stainless steel tube. The water flowing between the sintered stainless steel tube and the glass tube continuously strips sub-micron sized bubbles from the exterior surface of the sintered stainless steel tube.

Ultraviolet light energy from ultraviolet lamps is directed through the glass tube and engages the catalytic surface on the exterior of the sintered stainless steel tube, thereby forming hydroxyl radicals from the flowing water. The hydroxyl radicals homolytically cleave one of the carbon-hydrogen bonds in the methane to form either molecules of hydrogen or molecules of water, and methyl radicals. The methyl radicals combine either with the hydroxyl radicals to form methanol or with the hydrogen radicals to form methane.

The use of an internal semipermeable partition cylinder is shown in FIG. 1. One skilled in the art would also recognize that a vast number of shapes and orientations could be used to accomplish the same purpose. For example, glass tube 14 does not need to be shaped as a tube in order to be functional as a housing. In fact, such a housing need only be partially transparent to ultraviolet light for the apparatus to function. Additionally, the orientation of the methane inside an inner tube with water between the inner tube and a housing is not required. One skilled in the art could envision a housing bisected by a semipermeable partition creating a water chamber and a methane chamber. The only requirements of such an embodiment is that the water chamber has a water source and a product outlet, which leads to a methanol isolation apparatus, preferably a distillation apparatus; the methane chamber has a methane source; the semipermeable partition has a catalytic layer that is exposed to light energy on the water side of the partition; and the semipermeable partition allows the penetration of methane bubbles that are sheared off by the relative movement of water in the water chamber.

Figure 2:
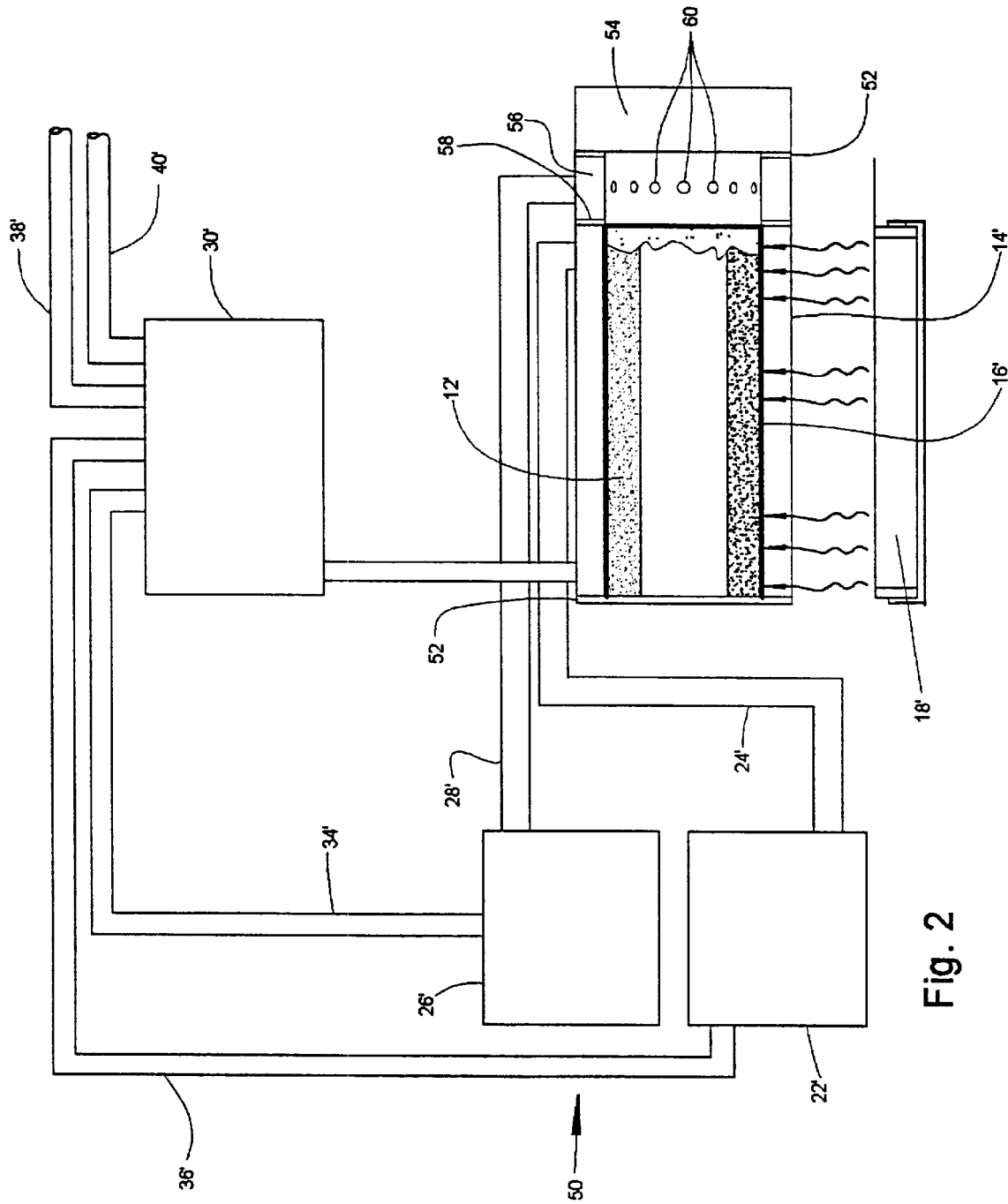
FIG. 2 is a diagrammatic illustration of a second embodiment of the apparatus of the present invention with a rotating sintered stainless steel tube.

Referring now to FIG. 2, there is shown an apparatus for manufacturing methanol comprising a second embodiment of the invention. The apparatus 50 comprises numerous component parts which are substantially identical in construction and function to the apparatus for manufacturing methanol 10 shown in FIG. 1 and described hereinabove in conjunction therewith. Such identical component parts are designated in FIG. 2 with the same reference numerals utilized in the description of the apparatus 10, but are differentiated therefrom by means of a prime (') designation.

In the apparatus for manufacturing methanol 50, the sintered stainless steel tube 12' is supported for rotation relative to the glass tube 14' by sealed bearings 52. Those skilled in the art will appreciate the fact that bearing/seal assemblies comprising separate components may be utilized in the practice of the invention, if desired.

A motor 54 is mounted at one end of the glass tube 14' and is operatively connected to the sintered stainless steel tube 12' to effect rotation thereof relative to the glass tube 14'. The glass tube 14' includes an end portion 56 which is isolated from the remainder thereof by a seal 58. The portion of the sintered stainless steel tube 12' extending into the end portion 56 of the glass tube 14' is provided with a plurality of uniform or nonuniform apertures 60.

In the operation of the apparatus for manufacturing methanol 50, methane is directed from the reservoir 26' through the piping 28' through the end portion 56 of the glass tube 14' and through the apertures 60 into the interior of the sintered stainless steel tube 12'. Water flows from the reservoir 22' through the piping 24' into the portion of the glass tube 14' that is isolated from the end portion 56 by the seal 58. Water flows out of the glass tube 14' through piping 32' to the distillation apparatus 30'.

The operation of the apparatus for manufacturing methanol 50 of FIG. 2 differs from the operation of the apparatus for manufacturing methanol 10 of FIG. 1 in that in the operation of the apparatus 50, the relative movement between the bubbles forming on the surface of the sintered stainless steel tube 12' and the water contained within the glass tube 14' is controlled by the motor 54 rather than the flow rate of the water as it passes through the glass tube 14'. This is advantageous in that it allows the sintered stainless steel tube 12' to be rotated at a relatively high velocity relative to the water contained within the glass tube 14', thereby assuring that sub-micron size bubbles will be sheared from the surface of the sintered stainless steel tube 12'. Meanwhile, the velocity of the water passing through the interior of the glass tube 12' can be relatively slow, thereby assuring a maximum number of sub-micron size bubbles entering the water per unit volume thereof.

Figure 3:
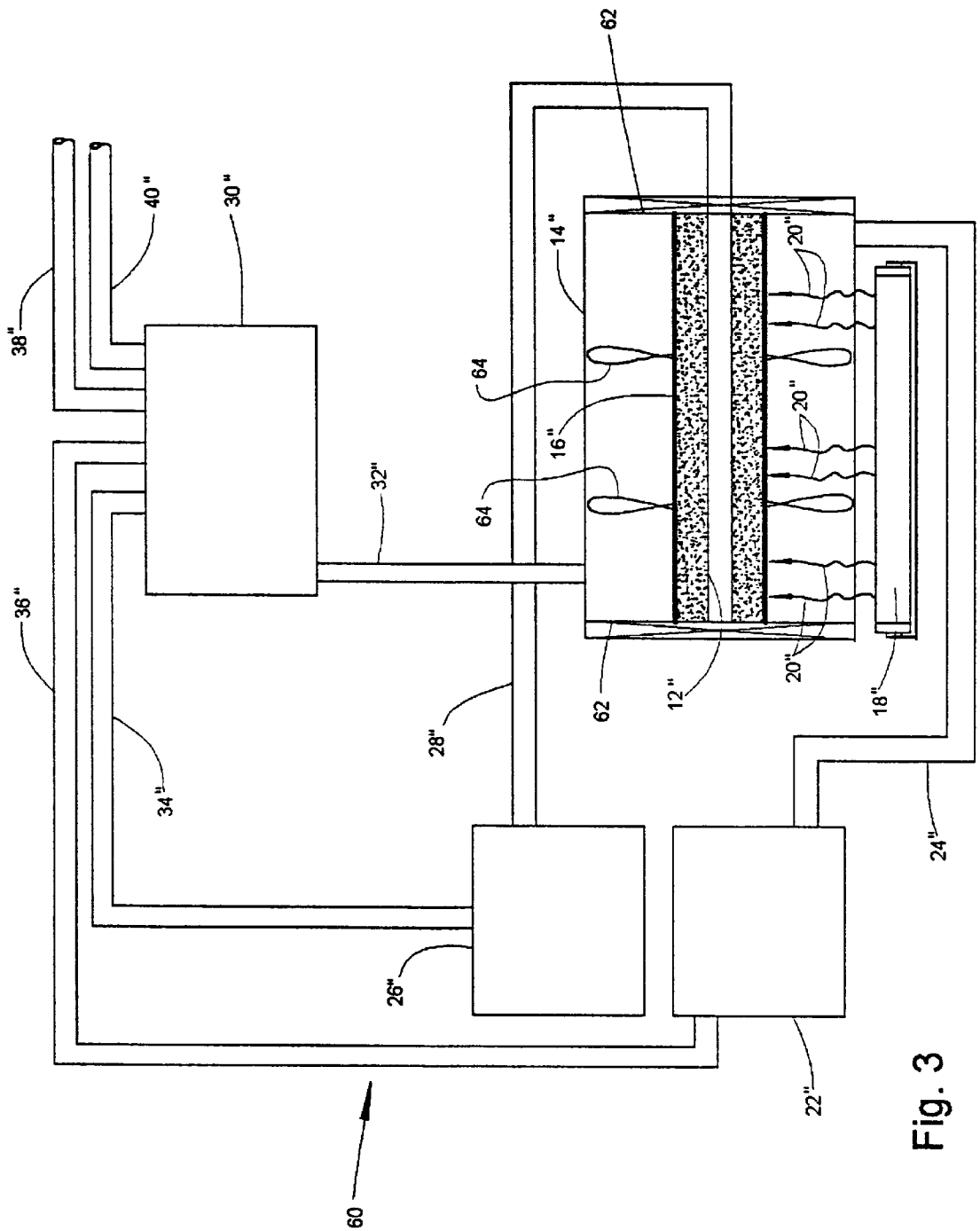
FIG. 3 is a diagrammatic illustration of a third embodiment of the apparatus of the present invention with a rotating sintered stainless steel tube with turbines.

An apparatus for manufacturing methanol comprising a third embodiment of the invention is illustrated in FIG. 3. The apparatus for manufacturing methanol 60 comprises numerous component parts which are substantially identical in construction and function to component parts of the apparatus for manufacturing methanol 10 illustrated in FIG. 1 and described hereinabove in conjunction therewith. Such identical component parts are designated in FIG. 3 with the same reference numerals utilized in the description of the apparatus 10, but are differentiated therefrom by means of a double prime (") designation.

The apparatus for manufacturing methanol 60 comprises a sintered stainless steel tube 12" which is supported for rotation relative to the glass tube 14" by sealed bearings 62. Those skilled in the art will appreciate the fact that the apparatus 60 may be provided with bearing/seal assemblies comprising separate components, if desired.

The sintered stainless steel tube 12" is provided with one or more turbines 64. The pitch of the turbines 64 is adjusted to cause the sintered stainless steel tube 12" to rotate at a predetermined speed in response to a predetermined flow rate of water through the glass tube 14".

Similarly to the apparatus for manufacturing methanol of FIG. 2, the use of the apparatus for manufacturing methanol 60 is advantageous in that the sintered stainless steel tube 12" can be caused to rotate relatively rapidly in response to a relatively low flow rate of water through the glass tube 14". This assures that sub-micron size bubbles will be stripped from the outer surface of the sintered stainless steel tube 12" and that a maximum number of bubbles will be received in the water flowing through the glass tube 14" per unit volume thereof. The use of the apparatus for manufacturing methanol 60 is particularly advantageous in applications of the invention wherein water flows through the system under the action of gravity, in that the use of the turbines 64 eliminates the need for a separate power source to effect rotation of the sintered stainless steel tube 12" relative to the glass tube 14".

Although preferred embodiments of the invention have been illustrated in the accompanying Drawings and described in the foregoing detailed description, it will be understood that the invention is not limited to the embodiments disclosed but is capable of numerous rearrangements, modifications, and substitutions of parts and elements without departing from the spirit of the invention.

I claim:
1. An apparatus for manufacturing methanol from methane comprising:
   a housing at least partially transparent to light;
   a gas permeable partition separating the interior of the housing into a reaction chamber and a methane chamber;
   a solid gas permeable photocatalytic layer formed on the gas permeable partition adjacent to the reaction chamber;
   means for directing light through the housing and into engagement with the photocatalytic layer;
   a product outlet opening out of the reaction chamber;
   a water source opening into the reaction chamber;
   means for continuously flowing water from the water source through the reaction chamber and through the product outlet;
   a methane source opening into the methane chamber;
   means for maintaining methane from the methane source within the methane chamber at a predetermined pressure sufficient to cause methane to continuously flow through the gas permeable partition and through the solid gas permeable photo catalytic layer for entrainment as sub-micron size bubbles in the flowing water while preventing water from flowing into the methane chamber; and
   a distillation apparatus in fluid communication with the product outlet.

2. The apparatus as recited in claim 1 wherein the distillation apparatus is in fluid communication with the water source such that water produced from the distillation apparatus is recycled into the water source; and additionally comprising a methane reservoir in gaseous communication with the distillation apparatus and the methane source such that unreacted methane is recycled into the methane source.

3. An apparatus for manufacturing methanol from methane comprising:
   a housing at least partially transparent to light from the source;
   a gas permeable tube inside of the housing, the gas permeable tube having an interior and an exterior, the gas permeable tube forming a reaction chamber between the housing and the exterior of the gas permeable tube;
   sealed bearings between the housing and the gas permeable tube allowing for rotation of the tube relative to the housing;
   a methane source opening into the interior of the gas permeable tube;
   a solid gas permeable photocatalytic layer formed at least on a portion of the exterior of the gas permeable tube;
   means for directing light through the housing and into engagement with the photocatalytic layer;
   a product outlet opening away from the reaction chamber;
   a water source opening into the to the reaction chamber;
   means for continuously flowing water from the water source through the reaction chamber and through the product outlet;
   means for maintaining methane from the methane source within the methane chamber at a predetermined pressure sufficient to cause methane to continuously flow through the gas permeable partition and through the photocatalytic layer for entrainment as sub-micron size bubbles in the flowing water while preventing water from flowing into the methane chamber; and means for rotating the gas permeable tube and the solid gas permeable photo catalytic layer thereon relative to the housing to further facilitate the entrainment of sub-micron size bubbles of methane in the flowing water.

4. The apparatus as recited in claim 3 additionally comprising turbines attached to the gas permeable tube to effect rotation thereof under the action of the flowing water.

5. The apparatus as recited in claim 3 wherein the semi-permeable tube comprises sintered stainless steel.

6. The apparatus as recited in claim 3 additionally comprising:

a distillation apparatus in fluid communication with the reaction outlet and the water source such that water produced from the distillation apparatus is recycled into the water source; and a methane reservoir in gaseous communication with the distillation apparatus and the methane source such that unreacted methane is recycled into the methane source.

* * * * *